United States Patent
Gautieri

(10) Patent No.: US 10,716,654 B2
(45) Date of Patent: Jul. 21, 2020

(54) INCONTINENCE CLAMP ASSEMBLY

(71) Applicant: Vito Gautieri, Batavia, NY (US)

(72) Inventor: Vito Gautieri, Batavia, NY (US)

( * ) Notice: Subject to any disclaimer, the term of this patent is extended or adjusted under 35 U.S.C. 154(b) by 401 days.

(21) Appl. No.: 15/690,444

(22) Filed: Aug. 30, 2017

(65) Prior Publication Data
US 2019/0060048 A1    Feb. 28, 2019

(51) Int. Cl.
*A61F 2/00* (2006.01)

(52) U.S. Cl.
CPC .... *A61F 2/0054* (2013.01); *A61F 2210/0057* (2013.01); *A61F 2220/0033* (2013.01); *A61F 2230/0065* (2013.01); *A61F 2250/0009* (2013.01); *A61F 2250/0018* (2013.01); *A61F 2250/0036* (2013.01); *A61F 2250/0063* (2013.01)

(58) Field of Classification Search
CPC ...... A61F 2/0004; A61F 2/005; A61F 2/0009; A61F 2/0013; A61F 2/0018; A61F 2/0054; A61F 2250/0013; A61F 13/2042; A61F 13/204; A61F 2002/30466; A61F 2002/30479; A61F 2002/30464; A61F 5/41; A61F 2/00; A61F 5/00; A61H 19/00; A61H 19/004; A61H 19/44; A61H 19/50; A61B 17/12
See application file for complete search history.

(56) References Cited

U.S. PATENT DOCUMENTS

| | | | |
|---|---|---|---|
| 2,699,781 A | | 1/1955 | Koch |
| 3,147,754 A | * | 9/1964 | Koessler ............... A61F 2/0054 128/885 |
| 3,203,421 A | * | 8/1965 | Arthur ................... A61F 2/0054 128/885 |
| 3,511,241 A | | 5/1970 | Lee |
| 3,623,481 A | * | 11/1971 | Curran ............... A61H 23/0263 601/74 |
| 4,239,044 A | | 12/1980 | Pavlinch |
| 4,880,016 A | * | 11/1989 | Worth ................... A61F 2/0054 128/885 |
| 4,942,886 A | * | 7/1990 | Timmons ............. A61B 17/132 128/885 |
| 5,397,294 A | * | 3/1995 | Hwang .................. A61H 19/50 601/70 |
| 6,039,750 A | * | 3/2000 | Kubalak ............... A61F 2/0054 128/DIG. 25 |
| 6,138,678 A | | 10/2000 | Nilsson |
| 6,349,727 B1 | * | 2/2002 | Stewart, Jr. .......... A61B 17/122 128/885 |

(Continued)

*Primary Examiner* — Alireza Nia
*Assistant Examiner* — Samuel B. Lum

(57) ABSTRACT

An incontinence clamp assembly includes a ring that may be worn on a penis. A tube is coupled to the ring. The tube is positioned on a bottom side of the penis having the tube being oriented perpendicular to the urethra. A stopper is slidably inserted into the tube and the stopper has a diameter that is larger than an inside diameter of the tube. The stopper is positioned in an open position having the stopper being positioned outside of the tube. In this way the stopper allows the urine to flow out of the penis. The stopper is positioned in a closed position having the stopper being positioned within the tube. In this way the stopper may compress the urethra thereby inhibiting urine from flowing out of the penis.

6 Claims, 3 Drawing Sheets

(56) References Cited

U.S. PATENT DOCUMENTS

| | | | | |
|---|---|---|---|---|
| 6,609,522 | B2 * | 8/2003 | Cheng | A61F 2/0054 |
| | | | | 128/885 |
| 7,108,668 | B2 * | 9/2006 | Fang | A61H 19/50 |
| | | | | 601/46 |
| D567,957 | S * | 4/2008 | Critchley | D24/105 |
| D589,610 | S | 3/2009 | Dubose, Jr. | |
| D601,710 | S * | 10/2009 | Klearman | D11/1 |
| 8,187,238 | B1 | 5/2012 | Dupree | |
| D674,910 | S * | 1/2013 | Adams | D24/215 |
| 8,641,000 | B1 * | 2/2014 | Eide | A47K 10/12 |
| | | | | 206/322 |
| 2003/0083598 | A1 * | 5/2003 | Kobayashi | A61F 5/41 |
| | | | | 601/70 |
| 2009/0204144 | A1 * | 8/2009 | De Francesco | A61B 17/122 |
| | | | | 606/201 |

\* cited by examiner

INCONTINENCE CLAMP ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to clamp devices and more particularly pertains to a new clamp device for PURPOSE.

BRIEF SUMMARY OF THE INVENTION

An embodiment of the disclosure meets the needs presented above by generally comprising a ring that may be worn on a penis. A tube is coupled to the ring. The tube is positioned on a bottom side of the penis having the tube being oriented perpendicular to the urethra. A stopper is slidably inserted into the tube and the stopper has a diameter that is larger than an inside diameter of the tube. The stopper is positioned in an open position having the stopper being positioned outside of the tube. In this way the stopper allows the urine to flow out of the penis. The stopper is positioned in a closed position having the stopper being positioned within the tube. In this way the stopper may compress the urethra thereby inhibiting urine from flowing out of the penis.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
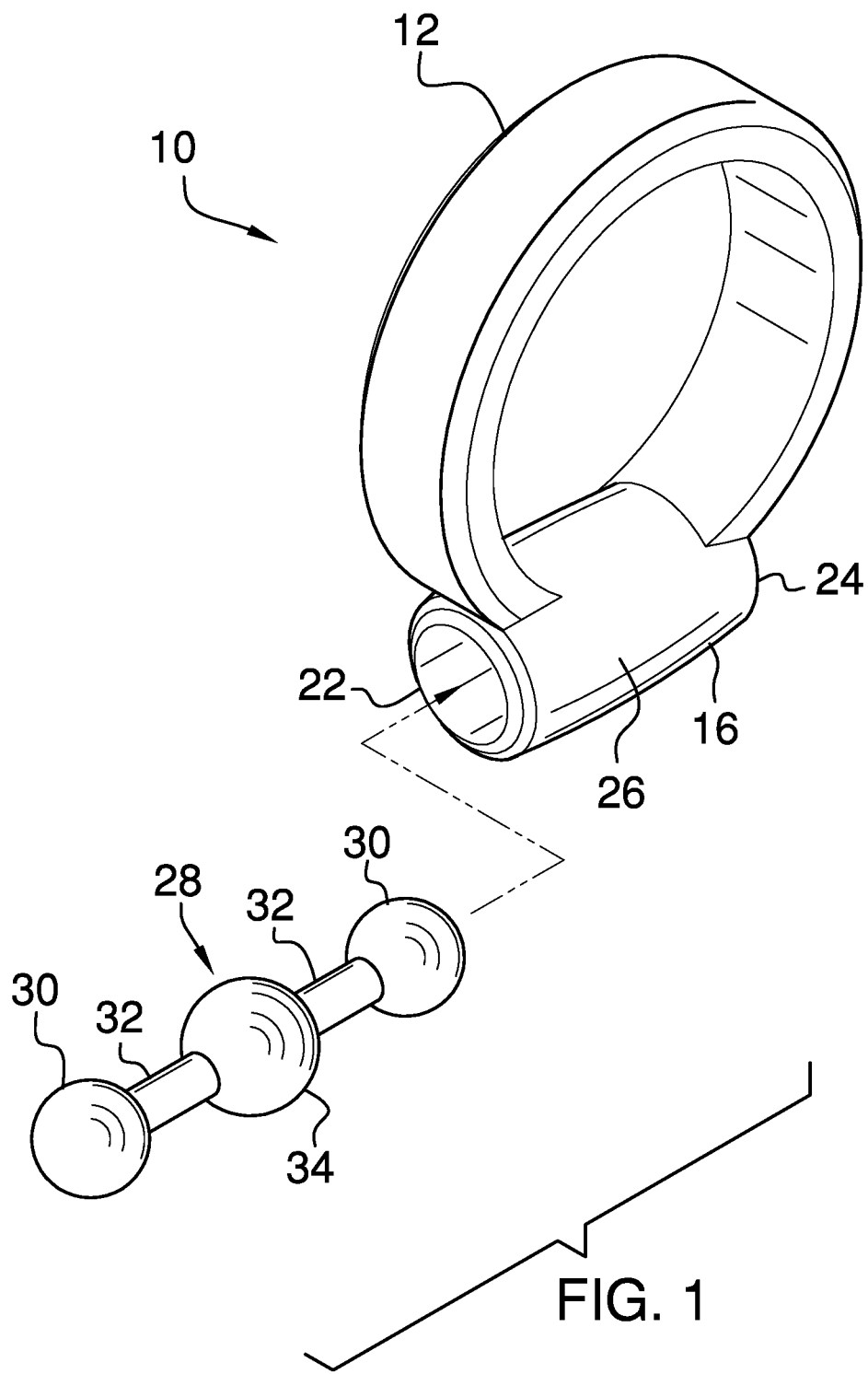
FIG. 1 is an exploded perspective view of an incontinence clamp assembly according to an embodiment of the disclosure.
Figure 2:
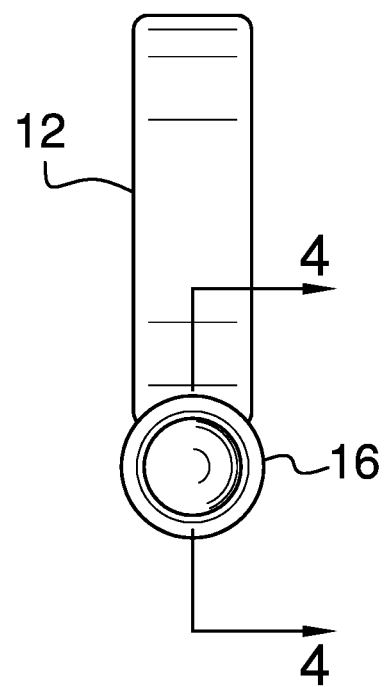
FIG. 2 is a right side view of an embodiment of the disclosure.
Figure 3:
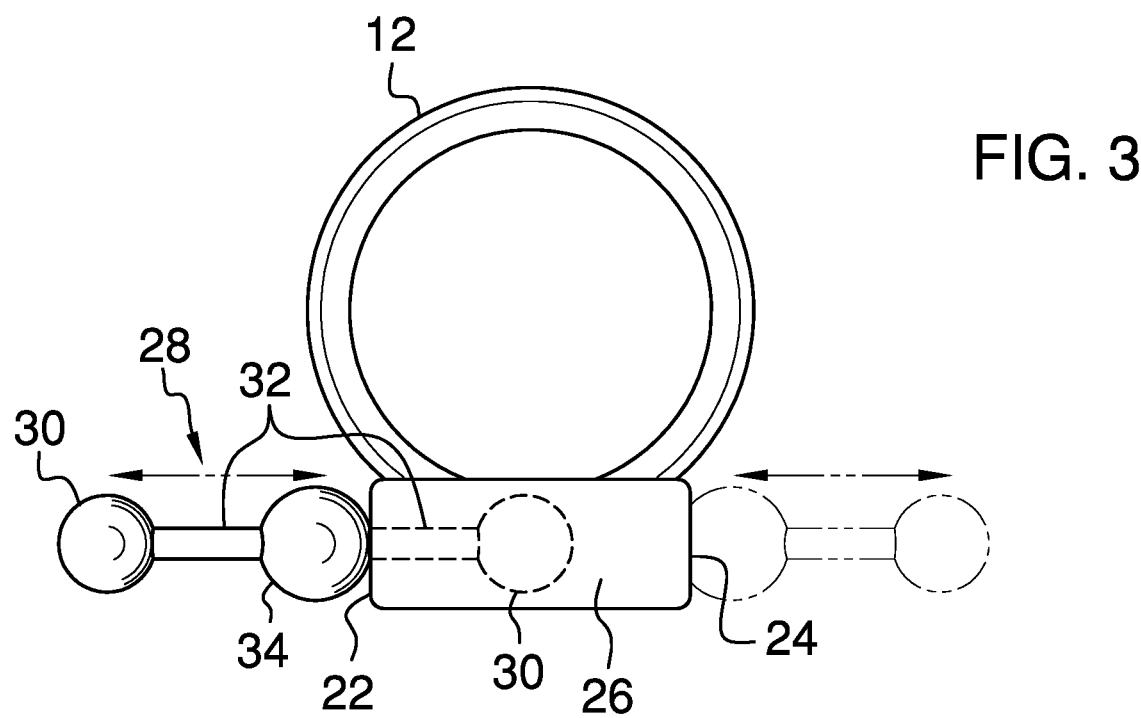
FIG. 3 is a front phantom view of an embodiment of the disclosure.
Figure 4:
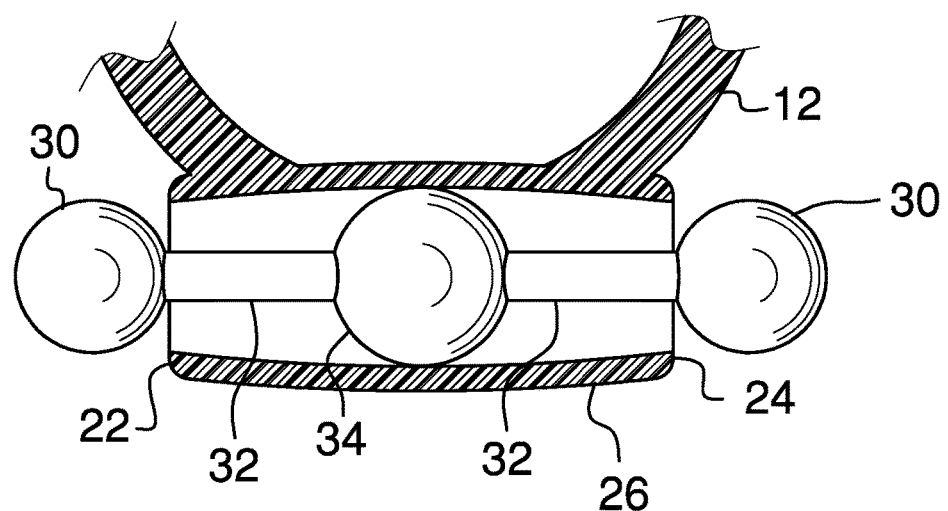
FIG. 4 is a cross sectional view taken along line 4-4 of FIG. 2 of an embodiment of the disclosure.
Figure 5:
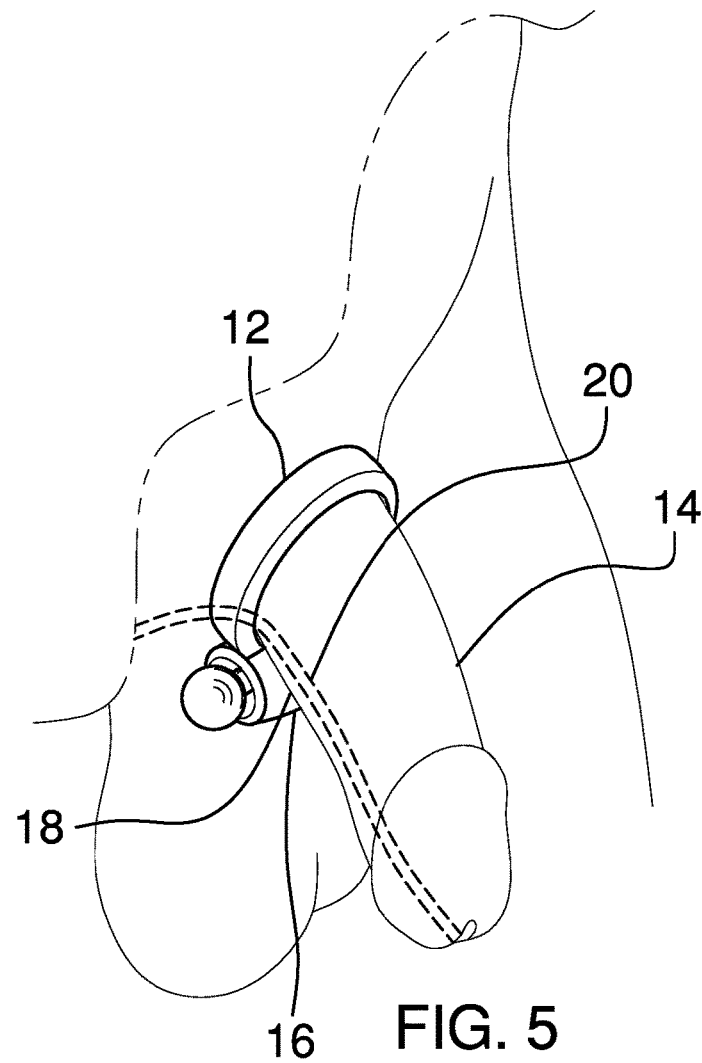
FIG. 5 is a perspective in-use view of an embodiment of the disclosure.

With reference now to the drawings, and in particular to FIGS. 1 through 5 thereof, a new clamp device embodying the principles and concepts of an embodiment of the disclosure and generally designated by the reference numeral 10 will be described.

As best illustrated in FIGS. 1 through 5, the incontinence clamp assembly 10 generally comprises a ring 12 that is worn on a penis 14. The ring 12 is comprised of a resiliently deformable material such as rubber or the like. A tube 16 is provided and the tube 16 is coupled to the ring 12. The tube 16 is positioned on a bottom side 18 of the penis 14 having the tube 16 being oriented perpendicular to the urethra 20. The tube 16 is comprised of a resiliently deformable material such as rubber or the like. The tube 16 has a first end 22, a second end 24 and an outer wall 26 extending therebetween. The ring 12 is coupled to the outer wall 26 such the outer wall 26 abuts the bottom side 18 of the penis 14.

A stopper 28 is provided and the stopper 28 is slidably inserted into the tube 16. The stopper 28 has a diameter that is larger than an inside diameter of the tube 16. The stopper 28 is positioned in a closed position having the stopper 28 being positioned within the tube 16. The stopper 28 compresses the urethra 20 thereby inhibiting urine from flowing out of the penis 14 when the stopper 28 is in the closed position. The stopper 28 is positioned in an open position having the stopper 28 being positioned outside of the tube 16. Thus, the stopper 28 allows the urine to flow out of the penis 14.

The stopper 28 comprises a pair of first balls 30 and each of the first balls 30 has a diameter that is less than the inside diameter of the tube 16. A selected one of the first balls 30 is positioned within the tube 16 when the stopper 28 is positioned in the open position. Moreover, the selected first ball 30 facilitates urine to flow through the urethra 20. The stopper 28 includes a pair of stems 32 and each of the stems 32 is coupled to and extends away from an associated one of the first balls 30.

A second ball 34 is coupled to each of the stems 32 such that the second ball 34 is positioned between each of the first balls 30. The second ball 34 has a diameter that is greater than the inside diameter of the tube 16. Moreover, the second ball 34 is positioned within the tube 16 when the stopper 28 is positioned in the closed position. In this way the second ball 34 compresses the urethra 20 thereby inhibiting urine from flowing through the urethra 20.

In use, the ring 12 is worn around the penis 14 of an incontinent user. The stopper 28 is inserted into the tube 16 having the second ball 34 being positioned in the tube 16. Thus, the second ball 34 causes the outer wall 26 of the tube 16 to stretch outwardly thereby compressing the urethra 20. In this way the stopper 28 inhibits urine from flowing out of the penis 14. A selected one of the first balls 30 is gripped and the second ball 34 is urged outwardly from the tube 16. Thus, the outer wall 26 of the tube 16 is no longer stretched outwardly to compress the urethra 20. In this way the stopper 28 allows the urine to flow out of the penis 14. The ring 12 and the stopper 28 reduces the need for urine absorbing pads and other products for incontinence.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An incontinence clamp assembly being configured to selectively restrict the flow of urine through a urethra, said assembly comprising:
a ring being configured to be worn on a penis;
a tube being coupled to said ring wherein said tube is configured to be positioned on a bottom side of the penis having said tube being oriented perpendicular to the urethra, said tube having a first end, a second end and an outer wall extending therebetween, said ring being coupled to said outer wall such said outer wall is configured to abut the bottom side of the penis; and
a stopper being slidably inserted into said tube, said stopper having a diameter being larger than an inside diameter of said tube, said stopper being positioned in an open position having said stopper being positioned outside of said tube wherein said stopper is configured to allow the urine to flow out of the penis, said stopper being positioned in a closed position having said stopper being positioned within said tube wherein said stopper is configured to compress the urethra thereby inhibiting urine from flowing out of the penis, said stopper comprising a pair of first balls, each of said first balls having a diameter being less than said inside diameter of said tube, a selected one of said first balls being positioned within said tube when said stopper is positioned in said open position wherein said selected first ball is configured to facilitate urine to flow through the urethra.

2. The assembly according to claim 1, wherein said tube is comprised of a resiliently deformable material.

3. The assembly according to claim 1, further comprising a pair of stems, each of said stems being coupled to and extending away from an associated one of said first balls.

4. The assembly according to claim 3, further comprising a second ball being coupled to each of said stems such that said second ball is positioned between each of said first balls.

5. The assembly according to claim 4, wherein said second ball has a diameter being greater than said inside diameter of said tube, said second ball being positioned within said tube when said stopper is positioned in said closed position wherein said second ball is configured to compress the urethra thereby inhibiting urine from flowing through the urethra.

6. An incontinence clamp assembly being configured to selectively restrict the flow of urine through a urethra, said assembly comprising:
a ring being configured to be worn on a penis, said ring being comprised of a resiliently deformable material;
a tube being coupled to said ring wherein said tube is configured to be positioned on a bottom side of the penis having said tube being oriented perpendicular to the urethra, said tube being comprised of a resiliently deformable material, said tube having a first end, a second end and an outer wall extending therebetween, said ring being coupled to said outer wall such said outer wall abuts the bottom side of the penis; and
a stopper being slidably inserted into said tube, said stopper having a diameter being larger than an inside diameter of said tube, said stopper being positioned in an open position having said stopper being positioned outside of said tube wherein said stopper is configured to allow the urine to flow out of the penis, said stopper being positioned in a closed position having said stopper being positioned within said tube wherein said stopper is configured to compress the urethra thereby inhibiting urine from flowing out of the penis, said stopper comprising:
a pair of first balls, each of said first balls having a diameter being less than said inside diameter of said tube, a selected one of said first balls being positioned within said tube when said stopper is positioned in said open position wherein said selected first ball is configured to facilitate urine to flow through the urethra,
a pair of stems, each of said stems being coupled to and extending away from an associated one of said first balls, and
a second ball being coupled to each of said stems such that said second ball is positioned between each of said first balls, said second ball having a diameter being greater than said inside diameter of said tube, said second ball being positioned within said tube when said stopper is positioned in said closed position wherein said second ball is configured to compress the urethra thereby inhibiting urine from flowing through the urethra.

* * * * *